United States Patent [19]

Kovac et al.

[11] Patent Number: 5,952,454

[45] Date of Patent: Sep. 14, 1999

[54] LINKING COMPOUNDS USEFUL FOR COUPLING CARBOHYDRATES TO AMINE-CONTAINING CARRIERS

[75] Inventors: Pavol Kovac, Silver Spring; Jian Zhang, Chevy Chase, both of Md.

[73] Assignee: The United States of America as represented by the Department of Health and Human Services, Washington, D.C.

[21] Appl. No.: 09/183,053

[22] Filed: Oct. 30, 1998

Related U.S. Application Data

[60] Provisional application No. 60/069,686, Dec. 12, 1997.

[51] Int. Cl.$^6$ .................................................. C08G 69/26
[52] U.S. Cl. ....................... 528/332; 528/339.3; 525/54.1
[58] Field of Search ................................ 528/332, 339.3; 525/54.1

[56] References Cited

U.S. PATENT DOCUMENTS

| | | | |
|---|---|---|---|
| 3,947,352 | 3/1976 | Cuatercasas et al. | 210/31 |
| 4,137,401 | 1/1979 | Lemieux et al. | 536/116 |
| 4,220,008 | 9/1980 | Sabesan | 60/602 |
| 4,356,170 | 10/1982 | Jennings et al. | 424/92 |
| 4,446,275 | 5/1984 | Filka et al. | 525/54.1 |
| 4,882,226 | 11/1989 | Schutyser et al. | 428/407 |
| 4,966,607 | 10/1990 | Shinoki et al. | 8/549 |
| 5,254,676 | 10/1993 | Sabesan | 536/4.1 |
| 5,424,297 | 6/1995 | Rubio et al. | 514/46 |

*Primary Examiner*—Terressa Mosley
*Attorney, Agent, or Firm*—Morgan & Finnegan, L.L.P

[57] ABSTRACT

The present invention provides a method to couple a glycosyl donor to an amine-containing carrier or substrate material using as a spacer a compound of the general formula I:

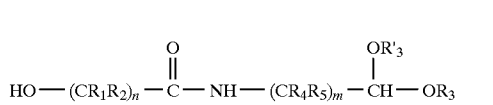

in which n and m are each independently an integer of from 1 to 12, $R_1$ and $R_2$ are each independently H, lower alkyl, a hydroxyl group, or a substituent which does not interfere with the linking reactions, $R_4$ and $R_5$ are each independently H, lower alkyl, a hydroxyl group, or a substituent which does not interfere with the linking reactions, $R_3$ and $R'_3$ are each independently an optionally substituted lower alkyl or $R_3$ and $R'_3$ can be joined to form an optionally substituted cyclic moiety having from 2 to 5 carbon atoms.

31 Claims, No Drawings

LINKING COMPOUNDS USEFUL FOR COUPLING CARBOHYDRATES TO AMINE-CONTAINING CARRIERS

This application claims benefit of Provisional Appl. No. 60/069,686, filed Dec. 12, 1997.

FIELD OF THE INVENTION

The present invention relates to compositions in which a carbohydrate is coupled to a carrier substrate containing an amine group by use of an organic spacer compound. The organic spacer compounds are compounds containing a group on one terminus which is attachable to a carbohydrate and a group at the other terminus attachable to the amine-containing carrier. The spacer compounds of the invention are heterobifunctional.

BACKGROUND OF THE INVENTION

Polymeric materials containing amino groups such as, for example, proteins and solid support-based organic and inorganic matrices (e.g. "aminopropyl glass") are often used as carriers of various materials including bioactive materials. Several methods are known for coupling carboxyl group-containing materials to such carriers.

The prior art has used coupling procedures to covalently link carboxylic group-containing biological macromolecules that are protective antigens of pathogenic bacteria. Acidic polysaccharides have been coupled to carrier proteins in order to form conjugate vaccines for increasing the immunogenicities of such polysaccharides. Another application is the coupling of acidic materials to solid carriers containing an amino groups for use in affinity chromatography. Such water-insoluble chromatographic media can be used, for example, for the isolation of antibodies from physiological fluids.

Another prior art method involves the activation of the carboxylic acid groups by hydroxysuccinimide derivatives. This method suffers from the same disadvantages as the carbodiimide procedure discussed, hereinabove.

A further known procedure employs adipic acid dihydrazide as a homobifunctional spacer. In the adipic acid dihydrazide method, the carboxylic acid group of a carbohydrate or polysaccharide is coupled to adipic acid dihydrazide in the presence of a water-soluble carbodiimide by way of the hydrazide linkage. The spacer is terminated by a strongly nucleophilic hydrazino group which can be coupled to the carboxylic acid group of a protein.

Potential disadvantages of this method include: (i) inter- and intramolecular crosslinking of the carboxylic acids group-containing carbohydrate or polysaccharide; and (ii) cross linking of the protein through its amino and carboxylic acid groups in the second phase of the conjugation.

U.S. Pat. No. 3,947,352 to Cuatercasas et al. discloses the periodate oxidation of polysaccharides and reaction of the aldehyde derivatives with polyhydrazide derivatives. The product of this reaction can then be coupled to various biologically active molecules.

Linkers or spacer compounds are also described by Fattom et al. Immunity, February 1992, pp. 584–589. The specific linkers disclosed by Fattom et al. are adipic acid dihydrazide and N-succinimidyl-3-(2-pyridyldithio) propionate. This article relates to the formation of conjugates of Staphylococcus aureus Type 8 capsular polysaccharide. The bond formed between these linkers and the capsular polysaccharide are identical. However, the N-hydroxysuccinimyl moiety reacts mostly with lysine amine groups of the protein while the hydrazide binds to the carboxyl in the protein.

U.S. Pat. No. 4,882,226 to Schutyser et al. relates to a carrier material which comprises a copolymeric core material which is covalently bonded to a hydrophilic coating material. The carboxyl groups on the core material are reacted with glycidol or glycidol derivatives and the hydrophilic material is linked directly to the core material or via various spacer groups.

U.S. Pat. No. 4,356,170 to Jennings et al. and U.S. Pat. No. 4,446,275 to Filka et al. teach procedures in which linking of polysaccharides is attained via the formation of an aldehyde moiety by periodate oxidation followed by coupling by reductive amination. This coupling is a direct linkage of the polysaccharide and the protein and would suffer from some of the same disadvantages as noted for the carbodiimide method, hereinabove. Additionally, this procedure requires the presence of vicinal hydroxy groups. Hence, oligosaccharide or polysaccharides which do not have vicinal hydroxyl groups cannot be coupled using this procedure. Care must be taken in order to prevent cross-linking during conjugate formation causing loss in conjugate solubility and activity.

The most successful of all carbohydrate pharmaceuticals so far have been the carbohydrate based, antibacterial vaccines [1]. The basis of using carbohydrates as vaccine components is that the capsular polysaccharides and the O-specific polysaccharides on the surface of pathogenic bacteria are both protective antigens and essential virulence factors. The first saccharide-based vaccines contained capsular polysaccharides of Pneumococci: in the United States a 14-valent vaccine was licensed in 1978 followed by a 23-valent vaccine in 1983. Other capsular polysaccharides licensed for human use include a tetravalent meningococcal vaccine and the Vi polysaccharide of *Salmonella typhi* for typhoid fever. The inability of most polysaccharides to elicit protective levels of anti-carbohydrate antibodies in infants and adults with weakened immune systems could be overcome by their covalent attachment to proteins that conferred T-cell dependent properties [2]. This principle led to the construction of vaccines against *Haemophilus influenzae* b (Hib) [3] and in countries where these vaccines are routinely used, meningitis and other diseases caused by Hib have been virtually eliminated. [4] Extension of the conjugate technology to the O-specific polysaccharides of Gram-negative bacteria provided a new generation of glycoconjugate vaccines that are undergoing various phases of clinical trials [5].

Chemical synthesis may provide fragments of natural polymers that have the necessary geometry to mimic conformational determinants of the native polymer which may be useful in diagnostics or as components of vaccines. The synthesis of di- to penta-, tetra-, hexa-, octa-, and dodeca-saccharide fragments of the O-specific polysaccharide of *Shigella dysenteriae* type 1 [6, 7] and the use of such synthetic oligosaccharides to map the carbohydrate binding specificity of anti O-specific polysaccharide specific murine monoclonal antibodies [8] have been previously reported. More recently, the synthesis of a hexadecasaccharide of *Shigella dysenteriae* type 1, consisting of consecutive tetrasaccharide repeating units, has been reported [9].

U.S. Pat. No. 4,137,401 to Lemieux et al. (1979) describes carbohydrate antigens with glycosidically linked bridging arms. The attachment chemistry for various conjugates is described in one embodiment of an attachment scheme as shown in Example XI, columns 17–19.

U.S. Pat. Nos. 4,220,008 and 5,254,676 to Sabesan (1993) describe inhibitors for influenza virus. The inhibitors are heptasaccharide compounds with various side chains (see column 2). In one embodiment, $R^1$ is $(CH_2)_n CONHR^3 NHC(O)R^4$.

Hallren and Hindsgaul, J. Carbohydrate Chem. (1995) describes linkers for fucose. In one embodiment, fucose is linked to biotin using a spacer.

Probert et al., Carbohydrate Res. (1996) describes various glycan epitopes. Synthetic carbohydrate molecules with side chains are shown.

U.S. Pat. No. 4,255,566 to Carrico and Johnson (1981) describes flavin adenine dinucleotide derivatives.

Jacobson et al., J. Med. Chem. (1987) describes adenosine conjugates where the structure of interest is used as a linker to peptides.

U.S. Pat. No. 5,424,297 to Rubio et al. (1995) describes conjugates of dextran with adenosine. FIG. 1C shows a conjugate where the structure of interest is used as the linker.

Larionova et al., Biol. Chem. (1985) describes the conjugation of aprotinin with dextran derivatives of D-galactose. The structure of interest is shown in Scheme 2.

Pozsgay et al., J. Org. Che. (1997) describes the conjugation of kojidextrins (oligosaccharides) to proteins. Side chains containing the structure of interest are shown.

Klyashchitsky and Mitina, J. Chromatography (1981) shows the use of the structure of interest in making affinity adsorbents.

Inman and Barnett, J. Chromatography (1986) describes the functionalization of agarose. The structure of interest is shown in FIG. 1 as a spacer.

U.S. Pat. No. 4,966,607 to Shinoki and Ono (1990) describes starch derivatives containing side chains (some of which have the structure of interest) for conjugation to dyes.

V. Pavliak, P. Kovac, C. P. J. Glaudemans, Synthesis of Ligans Related to the O-Specific Antigen of type 1 *Shigella Dysenteriae*. 2. Stereoselective syntheses of a di-, tri-, and a tetrasaccharide fragment of *Shigella dysenteriae* type 1 O-antigen using 3,4,6-tri-O-acetyl-2-azido- 2-deoxy-α-D-glucopyranosyl chloride as a glycosyl donor, Carbohydr. Res., 229 (1992) 103–116.

P. Kovac, K. J. Edgar, Synthesis of Ligands Related to the O-Specific Antigen of type 1 *Shigella Dysenteriae*. 3. Glycosylation of 4,6-O-substituted derivatives of methyl 2-acetamido-2-deoxy-α-D-glucopyranoside with glycosyl donors derived from mono- and oligosaccharides, J. Org. Chem., 57 (1992) 2455–2467.

P. Kovac, Synthesis of Ligands Related to the O-Specific Antigen of *Shigella Dysenteriae* type 1, 4. Enhanced stereoselectivity of α-D-galactosidation in the synthesis of the sequence α-D-gal-(1→3)-α-D-GlcNAc, allowing further extension of the chain at C-2', J. Carbohydr. Chem., 11 (1992) 999–1014.

P. Kovac, Di- and trisaccharide glycosyl donors for the synthesis of fragments of the O-specific antigen of *Shigella dysenteriae* type 1, Carbohydr. Res., 245 (1993) 219–231.

It is an object of the present invention to provide spacers for linking mono- oligo- or polysaccharides from which glycosyl donors can be made to amine-containing carriers, and a method of synthesis of such spacers.

It is a further object of the present invention to provide a coupling procedure in which an intermediate product can be isolated, purified and characterized prior to the coupling reaction.

It is yet a further object of the present invention to provide a heterobifunctional spacer or linking compound which can be used under mild chemical transformation conditions to carry out a coupling reaction.

A still further object of the present invention to provide a coupling procedure which does not adversely affect the structure or conformation of the materials which are coupled.

It is yet another object of the present invention to couple antigens based on natural, modified natural or synthetic mono- oligo- or poly-saccharides to an amine-containing carrier. It is also an object of the invention to couple molecules which are structurally related and/or antigenically similar to those mono- oligo- and poly-saccharides to a carrier material. Preferably, these mono- oligo- or poly-saccharides used in the invention are antigenically similar to known antigenic determinants.

It is yet another object of the present invention to provide mono- oligo- or poly-saccharide conjugates which are useful as vaccines.

SUMMARY OF THE INVENTION

According to the present invention, methods are provided to couple, substantially purified and/or synthesized natural, modified natural or synthetic mono- oligo- or polysaccharides or structurally related, immunologically similar mono-, oligo- or poly-saccharides to an amine-containing carrier or substrate material.

The above-noted and other objectives of the present invention are achieved by the use of spacer compound of the formula I:

(I)

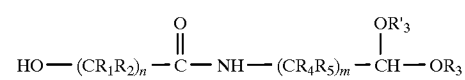

in which n and m are each independently an integer of from 1 to 12, $R_1$ and $R_2$ are each independently H, lower alkyl, a hydroxyl group, or a substituent which does not interfere with the linking reactions, $R_4$ and $R_5$ are each independently H, lower alkyl, a hydroxyl group, or a substituent which does not interfere with the linking reactions, $R_3$ and $R'_3$ are each independently an optionally substituted lower alkyl or $R_3$ and $R'_3$ can be joined to form an optionally substituted cyclic moiety having from 2 to 5 carbon atoms.

Spacer compounds of the formula I can be reacted with a glycosyl donor such as a suitable derivative of a mono, oligo- or polysaccharide to give a compound of the general formula II:

(II)

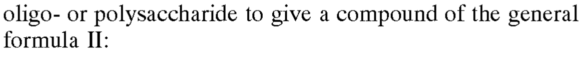

in which G is the radical of a glycoside such as a mono, oligo or polysaccharide and $R_1$, $R_2$, $R_3$, $R'_3$, $R_4$, $R_5$, n and m are the same as set forth hereinabove.

The linker compound of formula I is reacted with a carbohydrate to form a glycoside of formula II whose aglycon contains a masked aldehyde group which can be coupled to an amine-containing substrate. The protected material of formula (II) is sequentially deprotected, first in the carbohydrate moiety and then in the aldehyde function to create an aldehyde functionality at the end of the aglycon moiety and then the aldehyde group-containing material is reacted with a carrier material containing an amino group or a hydrazino group. The carrier may be any natural or synthetic material which contains a primary amino group and which is usually polymeric and which can be water-soluble, water-dispersible, or water-insoluble.

DETAILED DESCRIPTION OF THE INVENTION

The present invention relates to spacer or linker compounds useful in the linking of a mono, oligo- or polysaccharide to an amine group-containing substrate wherein the spacer compounds have the following general formula (I):

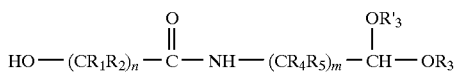
(I)

in which $R_1$, $R_2$, $R_3$, $R'_3$, $R_4$, $R_5$, n and m have the meanings given above. n is preferably 3–12 and more preferably 4–8 while m is preferably 1–10 and more preferably 1–3. Lower alkyls preferred in the present invention include optionally substituted $C_1$–$C_3$ alkyls preferably $C_1$–$C_2$ alkyls, in which the optional substituent is any radical which does not interfere with the linking reaction. It is preferred that the molecular weights of the spacer compounds of formula (I) be kept small in order to keep the boiling temperature low for vacuum distillation. The amine group-containing substrate has at least one amine group and has the following general formula (III):

(III)

in which $R_6$ is the residue of a carrier material, for example, a polysaccharide, lipopolysaccharide, oligopeptide, polypeptide or protein and q is an integer of 1 or greater; preferred carrier material is polypeptide or protein, most preferably protein. The spacer compound of formula I is linked to a carbohydrate such as a mono, oligo or polysaccharide via the hydroxyl group of the compound of formula I to form a material of the general formula II:

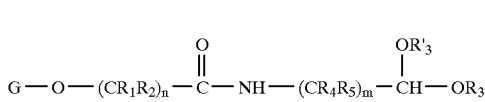
(II)

in which $R_1$, $R_2$, $R_3$, $R'_3$, $R_4$, $R_5$, n and m have the meanings given above.

The compound of formula (II) is deprotected sequentially first in the carbohydrate moiety and then in the aldehyde function to create an aldehyde functionality at the end of the aglycon moiety by known means to give an aldehyde of the general formula IV:

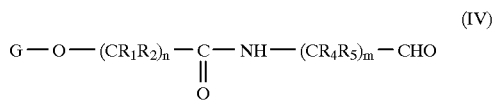
(IV)

in which $R_1$, $R_2$, $R_3$, $R'_3$, $R_4$, $R_5$, m and n have the meanings given above. Aldehydes of formula (IV) are then reacted with a carrier having at least one primary amino group of the general formula (III) to give a material of the general formula (V):

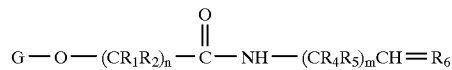
(V)

in which G, $R_1$, $R_2$, $R_4$, $R_5$, $R_6$, n and m have the meanings given above. Reduction of the material of formula (V) provides a product of the general formula (VI):

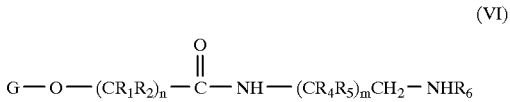
(VI)

in which G, $R_1$, $R_2$, $R_4$, $R_5$, $R_6$, n and m have the meanings given above.

Definitions:

"Oligosaccharide" as defined herein is a carbohydrate containing from two to ten simple sugar subunits linked together. A "polysaccharide" as defined herein is a carbohydrate containing more than ten simple sugar subunits linked together and can be prepared as a glycosyl donor. A generic mono-, oligo-, or polysaccharide is referred to herein as a carbohydrate or saccharide.

As used herein, "natural" refers to a native or naturally occurring mono- oligo- or polysaccharide which has been isolated from an organism, e.g., M. tuberculosis or M. bovis, and "modified natural" refers to native or naturally occurring mono-, oligo- or polysaccharide that has been structurally altered. Such structural alterations are any alterations that render the modified polysaccharide antigenically similar to an antigenic determinant.

In other words, a modified natural mono-, oligo- or polysaccharide as contemplated in this invention is characterized by its ability to immunologically mimic an antigenic determinant.

As used herein, the phrase "immunologically similar to" or "immunologically mimic" refers to the ability of a mono-, oligo- or polysaccharide to immunoreact with and/or to raise an antibody that recognizes and binds to a native antigenic determinant.

A mono-, oligo- or polysaccharide includes any substituted analog, fragment or chemical derivative (either natural or synthetic) so long as the mono-, oligo- or poly-saccharide is capable of reacting with antibodies that react with the parent antigen. Therefore, an oligo- or polysaccharide can be subject to various changes that provide for certain advantages in its use.

The terms "substitute", "substituted" and "substitution" include the use of a chemically derivatized residue in place of a non-derivatized residue provided that such modified oligo- or poly-saccharide display the requisite immunological activity. Such substituents can be any chemical group or moiety which does not substantially affect the linking reaction between the spacer compound and the glycosyl donor and the amine group-containing carrier.

"Chemical derivative" refers to a modified mono- oligo- or poly-saccharide having one or more residues chemically derivatized by reaction of a functional side group.

A "glycosyl donor" is a protected mono, oligo or polysaccharide with an activated anomeric end group that will react with hydroxyl group to form a glycoside.

Polymeric Carriers

Carriers are chosen on the basis of facilitating the function of increasing the immunogenicity of the mono- oligo- or polysaccharide. Carriers that fulfill these criteria are described in the art (10, 11, 12–15). Polymeric carriers can be a natural or a synthetic material containing a primary or/and a secondary amino group. The carrier can be water soluble or insoluble.

Polysaccharide carriers include, but are not limited to, *Haemophilus influenzae* type d polysaccharide, which contains an amino terminal.

Example of water insoluble carriers include, but are not limited to, aminoalkyl-Sepharose, e. g., aminopropyl or aminohexyl Sepharose, and aminopropyl glass and the like. Other carriers may be used when an amino group(s) is added through covalent linkage with a linker molecule by means known in the art.

Trial carriers include bovine serum albumin, and chicken serum albumin. Examples of carriers for vaccine are natural peptides and proteins such as diphtheria toxoid, tetanus toxoid, *Pseudomonas aeruginosa* recombinant ex: protein A, Clostridium perfringens exotoxins, pertussis vaccine (LPF toxoid), tubercular bacilli vaccine, cross-reacting materials (CRM's) which are antigenically similar to bacterial toxins but are non-toxic by means of mutation, preferably CRM 197 obtained according to Pappenheimer, et al., Immunochemistry, 9, 891–906 (1972) and other bacterial protein carriers, for example meningococcal outer membrane protein. When a vaccine is being prepared the substrate protein can itself be an immunogen. Further substrate materials include immunogenic proteins derived by bacteria such as β-hemolytic streptococci, Haemophilus influenza, meningococci, pneumococci and *E. coli*. Other substrates may also be used in which the substrate has been modified to contain a chemically linked amino group, for example polysaccharides to which an aminoalkyl group is attached through a covalent linkage.

Dosage for Vaccination

Inoculum or vaccine within the scope of this invention contains an effective, immunogenic amount of mono- oligo- or poly-saccharide conjugate of this invention. The effective amount of mono- oligo- or poly-saccharide carrier conjugate per unit dose sufficient to induce an immune response depends on the species of mammal inoculated, the body weight of the mammal and the chosen inoculation regimen as is well known in the art. Inocula typically contain mono- oligo- or poly-saccharide carrier conjugates with concentrations of mono- oligo- or poly-saccharide of about 1 microgram to about 100 milligrams per inoculation (dose), preferably about 3 micrograms to about 100 micrograms per dose, most preferably about 5 micrograms to 50 micrograms.

The administration of the agents of the invention may be for either "prophylactic" or "therapeutic" purpose. When provided prophylactically, the agents are provided in advance of any symptom. The prophylactic administration of the agent serves to prevent or ameliorate any subsequent infection. When provided therapeutically, the agent is provided at (or shortly after) the onset of a symptom of infection. The agent of the present invention may, thus, be provided either prior to the anticipated exposure (so as to attenuate the anticipated severity, duration or extent of an infection and disease symptoms) or after the initiation of the infection.

For all therapeutic, prophylactic and diagnostic uses, the mono- oligo- or polysaccharide linked to a carrier and other necessary reagents and appropriate devices and accessories may be provided in kit form so as to be readily available and easily used.

The carbohydrates useful in the present invention include, inter alia, mono, oligo, and polysaccharides and saccharide fragments of lipolysaccharides. It is contemplated that virtually any mono, oligo- or polysaccharide or fragment of a lipopolysaccharide can be used in the present invention the only limitation being the ability to convert such carbohydrates into glycosyl donors.

Examples of carbohydrates of polysaccharides that either are or could be converted into glycosyl donors and used in conjunction with the linker of the present invention include, but are not limited to, those whose preparation is described in:

P. Kovac, K. J. Edgar, Synthesis of Ligands Related to the O-Specific Antigen of type 1 *Shigella Dysenteriae*. 3. Glycosylation of 4,6-O-substituted derivatives of methyl 2-acetamido-2-deoxy-α-D-glucopyranoside with glycosyl donors derived from mono- and oligo-saccharides, J. Org. Chem., 57 (1992) 2455–2467.

Laferriere, C. A., Sood, R. K., Muys, J. M., Michon, F. Jennings, H. J., The Synthesis of Streptococcus pneumoniae polysaccharide-tetanus toxoid conjugates and the effect of chain length on immunogenicity, Vaccine, 15 (1997) 179–186.

P. Kovac, Di- and trisaccharide glycosyl donors for the synthesis of fragments of the O-specific antigen of *Shigella dysenteriae* type 1, Carbohydr. Res., 245 (1993) 219–231.

Jian Zhang and P. Kovac, Synthesis of Methyl α-Glycosides of Some Higher oligosaccharide Fragments of the O-Antigen of Vibrio Cholera 01, Stereotype Inaba and Ogawa, Carbohydr. Res., Vol. 300, 1997, p.329–339.

Ping-Sheng Lei, Yuji Ogawa, Paul Kovac, Synthesis of Methyl-α-Glycosides of A Di-, Tri-, and Tetrasaccharide Fragment Mimicking the Terminus of the O-Polysaccharide of Vibrio Cholera 01, Sterotype Inaba and Ogawa, Carbohydr. Res., Vol. 281, 1996, p. 47–60.

In the present invention, the spacer is a hydroxyl group containing a protected aldehyde of the general formula I shown hereinabove. The present compounds of formula I are prepared by the following reaction sequence:

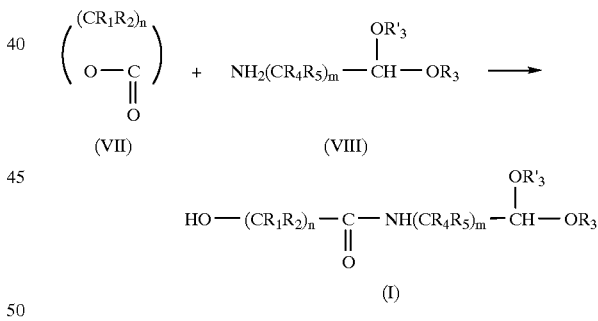

$R_1$, $R_2$, $R_3$, $R'_3$, $R_4$ and $R_5$ as well as n and m have the meanings given hereinabove.

Illustrative lactones of formula VII include but are not limited to ε-caprolactone, δ-butyrolactone and δ-caprolactone. The compounds of formula VIII are amines containing masked aldehyde groups. Compounds of formula VII and VIII are made by means well known in the art. The amine aldehydes can be prepared by reduction of amino acids or the controlled oxidation of amino alcohols. The amine aldehydes and their protected counterparts are known compounds or are readily prepared by the ordinary artisan.

The method according to the present invention comprises a method for the coupling of a mono-, oligo-, poly- or lipopoly-saccharide to an amino group-containing material through the spacer compounds of formula I. The method comprises the steps of:

a) providing a glycosyl donor derived from a mono-, oligo-, poly- or a saccharide fragment of a lipopolysaccharide;

b) reacting the glycosyl donor with a linker of formula I to give an intermediate in which a residue of the protected saccharide is coupled to the linker compound via its hydroxyl group;

b') subjecting the intermediate of step b) to deprotection of the saccharide to generate an intermediate having the saccharide moiety deprotected but the aldehyde function still protected;

c) subjecting the intermediate of step b') to deprotection to generate a terminal adehydo group;

d) selecting an amino group-containing carrier material having at least one primary amino group and reacting the amino group of the carrier material with the aldehydo group of the material formed in step c) to provide a Schiff base;

e) reducing the Schiff base of step d) and;

f) isolating the linker coupled material.

The coupling of the aldehydo group-containing material to the amino group-containing carrier is referred to as reductive amination.

The hydroxyl group in the linkers can be glycosylated using any of the glycosyl donors known to those skilled in the art, such as glycosyl halides (prepared as described in [16–18]) thioglycosides (prepared as described in [19], glycosyl imidates (prepared as described in [20]) and other carbohydrate derivatives (such as those found in [21, 22]). Protected glycosyl donors are prepared from acylated, preferentially acetylated or benzoylated, saccharides (prepared as described in [23]), or benzylated saccharides (prepared as described in [24]). The glycosylation itself is performed as described in [18–20, 25–36], yielding fully protected, linker equipped saccharides. After deacylation (performed as described in [23]) or debenzylation (performed as described in [37]) in the saccharide moiety, the obtained compound is a saccharide glycoside whose aglycon contains a masked aldehyde group in the form of dialkyl acetal. Hydrolysis of the dialkyl acetal with dilute hydrochloric or trifluoroacetic acid (as described in [38–39]) then yields a glycoside whose linker contains the free aldehyde group, making it thus amenable to coupling to proteins by reductive amination.

The coupling of linker to the saccharide can be verified, for example, by mass spectroscopy or by nuclear magnetic resonance methods by comparing the integral intensities of the characteristic signals of the linker to those of the saccharide. Optimum conditions for the coupling reaction are quite readily determinable. It is preferable to use excess linker in order to enhance production of desired product.

Unreacted linker and by-products of the reaction can be removed from the glycoside by known methods of separation, e.g., crystallization or chromatography.

The coupling of the aldehydo group containing material with the amino group-containing carrier material is performed in an aqueous solution at a pH close to neutral, for example, at a pH of between about 6 to 9. An intermediate imine (Schiff-base) is formed which is stabilized by reduction with a mild reducing agent such as, for example, sodium borohydride or sodium cyanoborohydride. This, procedure is often referred to as reductive amination. (See Gray, G. Arch. Biochem. Biophys, 1974, 163, pp 426–428). Other reducing agents can be employed, for example, borane-pyridine reagent. (See Cabacungan et al., Anal. Biochem., 1982, 124, pp 272–278).

The degree of coupling of the aldehydo group-containing material and the amino group-containing carrier material is adjusted by varying the ratio of the aldehydo group containing material to the carrier material. Removal of excess reagent and final purification of the conjugate is achieved by known methods of purifications such as, for example, by dialysis and gel chromatography. When a solid water-insoluble carrier material is used, purification is achieved by washing the solid product particles with water.

The amount of the saccharide in the conjugate is determined by known methods. In the case of saccharide coupling, carbohydrate analysis, for example by the phenolsulfuric acid assay can be employed. (See Chaplin et al., Carbohydrate Analysis, a practical approach, IRL Press, Oxford, Washington, 1986) or by MALDI TOF mass spectroscopy.

The conjugates of the present invention are useful as vaccines or as components in multiple vaccines. The vaccines including one or more conjugates comprise a liquid carrier such as physiological saline or other injectable liquids. Additives customarily used in such vaccines may be present e.g. stabilizers such as lactose or sorbitol and adjuvants such as aluminum hydroxide, sulfate or phosphate, an alum or an alginate. Precipitated $AlPO_4$ is also suitable.

The vaccines may be administered by injection, usually intramuscularly, subcutaneously or intravenously. The amount of conjugate is the effective amount needed to obtain the desired immunological effect and can be, for example, from between about 1 to 100 micrograms/ml, preferably about 5 to 40 micrograms/ml. The dosage will depend upon the host receiving the vaccine as well as factors such as the size, weight and age of the host. Depending upon the material used, the present vaccines are useful in both humans and animals.

The vaccine compositions of this invention may be stored in lyophilized form and reconstituted in a physiologically acceptable vehicle to form a suspension prior to administration. Alternatively, the vaccine can be stored in the vehicle. Preferred vehicles include sterile solutions, in particular, sterile buffer solutions, such as phosphate buffered saline.

The vaccine may contain preservatives or other known additives which are used to improve the shelf stability or the efficacy of the mixture. Suitable preservatives include, for example, thimerosal.

The volume of a single dose of the vaccine may vary but will be generally within the ranges commonly employed in conventional vaccines. The volume of a single dose is preferably between the 0.1 ml and about 1.5 ml, more preferably between about 0.2 ml and about 0.5 ml at the concentration of conjugate noted above.

The following examples are illustrative of the present invention and should not be deemed limiting in any way.

EXAMPLE 1

An illustrative preparation of spacers useful in this invention includes the reaction of three commercially available amines with the readily available 6-hexanolactone ($\epsilon$-caprolactone):

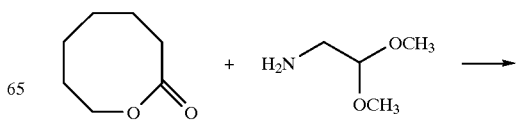

11

-continued

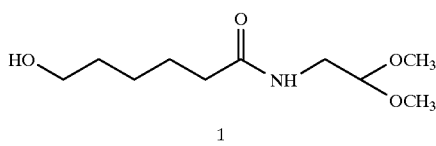

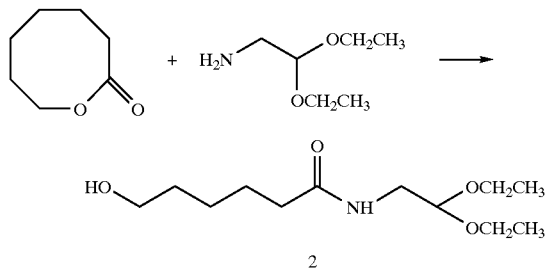

12

-continued

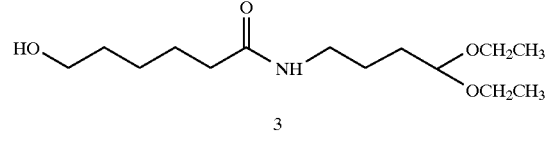

Products 1, 2 and 3 are conveniently obtained by treatment of the amine containing protected aldehyde with excess lactone at room temperature until satisfactory conversion is achieved (3–7 days). 1, 2 and 3 are isolated from the crude reaction mixtures by fractional vacuum distillation.

EXAMPLE 2

Preparation of a neoglycoconjugate from the monosaccharide antigen fragment of the O-polysaccharide (O-PS) of *Vibrio cholerae* 0:1

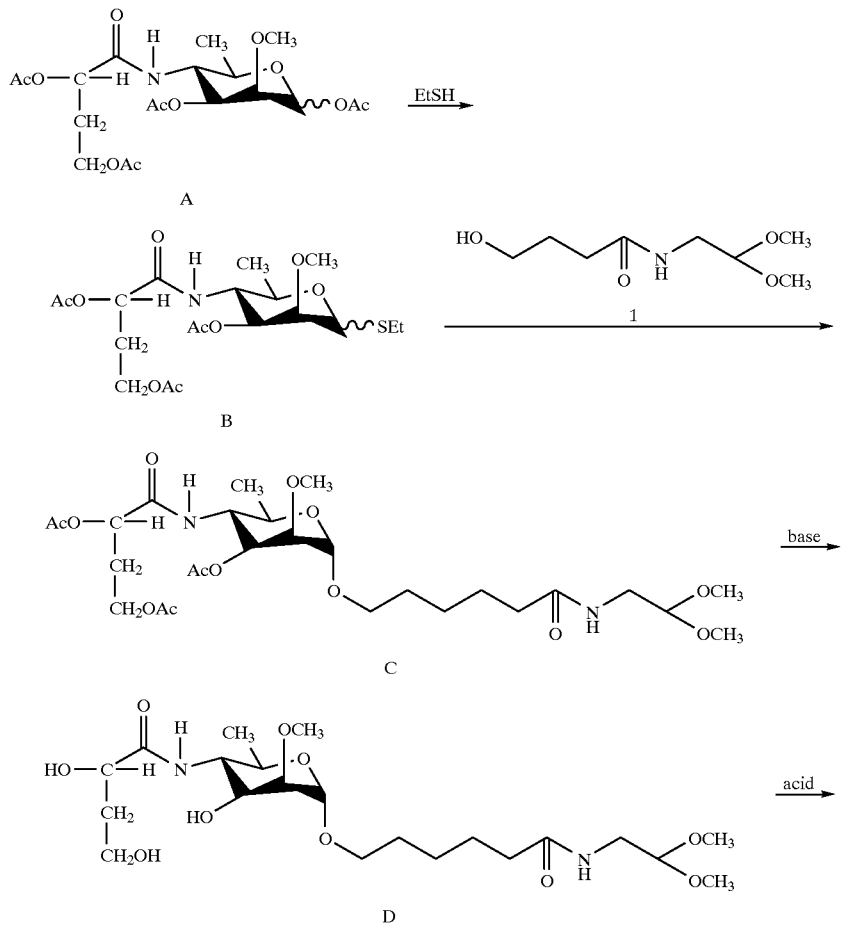

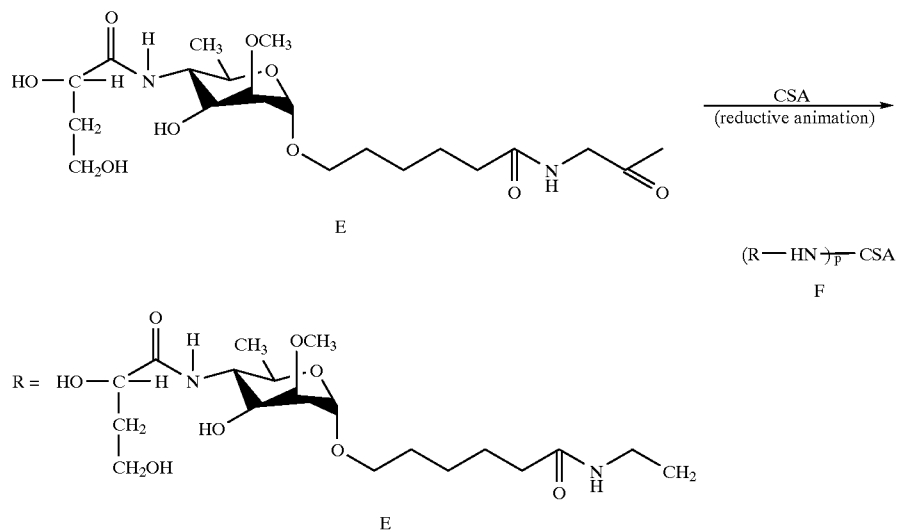

This example describes the synthesis of a neoglycoconjugate based on the monosaccharide antigen representing the terminal, non-reducing moiety of the O-specific polysaccharide of *Vibrio cholerae* 0:1 serotype Ogawa, equipped with a heterobifunctional linker, which provides the attachment of the monosaccharide ligand to chicken serum albumin (CSA) as a model carrier protein. The monosaccharide has been shown (Wang, J., Zhang, J., Miller, C. E., Villenuve, S., Ogawa, Y., Lei, P.-s., Lafaye, P., Nato, F., S. Szu, Bystricky, S., Karpas, A., robbins, J. B., Kovac, P., Fournier, J. M., Glaudemans, C. P. J. On the antigenic determinants of the lipopolysaccharides of *Vibrio cholerae* 0:1, serotypes Ogawa and Inaba, J. Biol. Chem., in press.) to be the immunologically dominant epitope in the O-PS. It is believed that such determinants, when linked to suitable carriers could be used as vaccines to elicit O-PS-specific, protective antibodies. The single-point attachment preserves the structural integrity of the monosaccharide and makes it available unchanged for interaction with the elements of the immune system. The average number of saccharide chains attached to CSA is defined by MALDI TOF mass spectrometry. In the reaction scheme, the number "p" of saccharide claims can be from 1 to about 46 depending on the coupling conditions, i.e., the time of reaction and/or molar ratio of reactants. The overall strategy of the target neoglycoconjugate F involves the use of the fully acetylated derivative A (prepared as described in Lei, P. S., Ogawa, Y., and Kovac, P., Synthesis of a di-, tri- and a tetrasaccharide fragment mimicking the terminus of the O-polysaccharide of *Vibrio cholerae* 0:1, serotype Ogawa, Carbohydr. Res., 281 (1996) 47–60) as the starting material. Thus, boron trifluoride etherate (0.1 mL, 1 equiv.) was added to a solution of ethane thiol (94 mmol, 100% molar excess) and A (340 mg, 0.76 mmol), and the solution was stirred at room temperature for 20 min. After conventional processing, chromatography yielded the glycosyl donor B in 93% yield as a mixture of anomers.

N-Iodosuccinimide (135 mg 0.6 mmol), followed by silver trifluoromethanesulfonate (13 mg, 0.05 mmol) was added to a mixture of B (225 mg, 0.5 mmol), dimethyl acetal 1 (132 mg, 0.6 mmol) and molecular sieve 4 Å (200 mg) that had been stirred for 15 min. The conversion of the thioglycoside was virtually one-product-forming, instantaneous, as shown by thin-layer chromatography, and leaving only little of unchanged B. Compound C was obtained in 88% yield by chromatography.

Deacetylation of C, by standard Zemplen procedure (Thompson, A., and Wolfrom, M. L., Methods Carbohydr. Chem., 2 (1963) 216–220) gave D in virtually theoretical yield.

A solution of D (11 mg 23 μmol) in 0.05 M trifluoroacetic acid (2 mL) was heated at 100° C. for 20 min. After concentration, and evaporation of water from the residue, the obtained aldehyde E was treated, for 5 days at pH=7, with CSA (16 mg. 0.24 μmol) in the presence of sodium cyanoborohydride, as described [Gray, G. R., Schwartz, B. A., Kamicker, B. J. Prog. Biol. Res., 23 (1978) 583–94], After exhaustive dialysis and filtration through a 0.45 μm syringe filer, the freeze-dried material (12 mg) contained 14 residues of the linker-equipped monosaccharide ligand for each CSA.

REFERENCES

[1] For reviews, see:
  (a) J. B. Robbins, R. Schneerson, S. Szu, V. Pozsgay, In: *Vaccinia, vaccinations and vaccinology: Jenner, Pasteur and their successors* (Ed.: S. Plotkin, B. Fantini), Elsevier, Paris, 1996, p. 135–143.
  (b) R. K. Sood, A. Fattom, V. Pavliak, R. B. Naso, *Drug Discovery Today* 1996, 1, 381–387.
  (c) A. Fattom, Adv. Expt. Med. Biol. 1995, 383, 131–139.
  (d) U. B. S. Sørenson, *Danish Med. Bull.* 1995, 42, 47–53.
  (e) H. J. Jennings, R. K. Sood, In *Neoglycoconjugates. Preparation and Applications* (Eds. Y. C. Lee, R. T. Lee), Academic Press, New York, 1994, pp. 325–371.
  (f) W. Egan, *Ann. Rep. Med. Chem.* 1993, 28, 257–265.
  (g) P. R. Paradiso, K. Dermody, S. Pillai, *Vaccine Research* 1993, 2, 239–248.
  (h) H. J. Jennings, *Curr. Top. Microbiol. Immunol.* 1990, 150, 97–127.

[2] For the development of this concept, see:
  (a) K. Landsteiner, *The specificity of serological reactions*, Harvard University Press, Cambridge, 1970.
  (b) W. F. Goebel, O. T. Avery, *J. Exp. Med.* 1929, 50, 521–531.

[3] R. Schneerson, O. Barrera, A. Sutton, J. B. Robbins, *J. Exp. Med.* 1980, 152, 361–376.

[4] J. B. Robbins, R. Schneerson, P. Anderson, D. H. Smith, *J. Am Med. Assoc.* 1996, 276, 1181–1185.

[5] For example:
(a) D. Cohen, S. Ashkenazi, M. S. Green, M. Gdalevich, G. Robin, R. Slepon, M. Yavzori, N. Orr, C. Block, Y. Ashkenazi, J. Schemer, D. N. Taylor, T. L. Hale, J. D. Sadoff, D. Pavliakova, R. Schneerson, J. B. Robbins, *Lancet*, 1997, 349, 155–0159.
(b) D. Cohen, S. Ashkenazi, M. S. Green, Y. Lerman, R. Slepon, G. Robin, N. Orr, D. N. Taylor, J. C. Sadoff, C. Chu, J. Shiloach, R. Schneerson, J. B. Robbins, *Infect. Immun.* 1997, 64, 4074–4077.

[6]
(a) V. Pozsgay, B. Coxon, *Carbohydr. Res.* 1995, 277, 171–178.
(b) V. Pozsgay, L. Pannell, *Carbohydr. Res.* 1994, 258, 105–122.
(c) V. Pozsgay, B. Coxon, *Carbohydr. Res.* 1994, 257, 189–215.
(d) V. Pozsgay, B. Coxon, H. Yeh, *Bioorg. Med. Chem.* 1993, 1, 237–257.
(e) V. Pozsgay, C. P. J. Glaudemans, J. B. Robbins, R. Schneerson, *Carbohydr. Res.* 1993, 244, 259–273.
(f) V. Pozsgay, C. P. J. Glaudemans, J. B. Robbins, R. Schneerson, *Tetrahedron* 1992, 48, 10249–10264.

[7] V. Pozsgay, C. P. J. Glaudemans, J. B. Robbins, R. Schneerson, *Biorganic & Medicinal Chem. Lett.*, 1992, 2, 255–260.

[8]
(a) V. Pavliak, J. Nashed, V. Pozsgay, P. Kovac, A. Karpas, C. Chu, R. Schneerson, J. B. Robbins, and C. P. J. Glaudemans, *J. Biol. Chem.*, 1993, 268, 25797–25802.
(b) C. E. Miller, R. Schneerson, K. Huppi, A. Karpas, P. Kovac, V. Pozsgay and C. P. J. Glaudemans, Mol. Immunol. Mol. Immunol. 1996. 33, 1217–1222.

[9] V. Pozsgay, J. Amer. Chem. Soc. 1995, 117, 6673–6681.

[10] Devi, S. J., J. B. Robbins and R. Schneerson. 1992. Antibodies to poly[(2→8)-α-N-acetylneuraminic acid] are elicited by immunization of mice with *Escherichia coli* K92 conjugates: Potential vaccines for groups B and C meningococci and *E. coli*. Proc. Natl. Acad. Sci. USA 88:7175–7179, 1991.

[11] Fattom, A., C. Lue, S. C. Szu, J. Mestecky, G. Schiffman, D. A. Bryla, W. F. Vann, D. Watson, L. M. Kimzey, J. B. Robbins, and R. Schneerson. (1990) Serum antibody response in adult volunteers elicited by injection of *Streptococcus pneumoniae* type 12F polysaccharide alone or conjugated to diphtheria toxoid. Infect. Immun. 58:2309–2312

[12] Szu, S. C., X. Li, R. Schneerson, J. H. Vickers, D. Bryla, and J. B. Robbins. 1989. Comparative immunogenicities of Vi polysaccharide-protein conjugates composed of cholera toxin or its B subunit as a carrier bound to high- or lower-molecular-weight Vi. Infect. Immun. 57:3823–3827.

[13] Szu, S. C., X. Li, A. L. Stone, and J. B. Robbins. 1991. Relation between structure and immunologic properties of the Vi capsular polysaccharide. Infect. Immun. 59:4555–4561.

[14] Szu, S. C., A. L. Stone, J. D. Robbins, R. Schneerson, and J. B. Robbins. 1987. Vi capsular polysaccharide-protein conjugates for prevention of typhoid fever. *J. Exp. Med.* 166:1510–1524.

[15] Szu, S. C., D. N. Taylor, A. C. Trofa, J. D. Clements, J. Shiloach, J. C. Sadoff, D. A. Bryla and J. B. Robbins. 1994. Laboratory and preliminary clinical characterization of Vi capsular polysaccharide-protein conjugate vaccines. Infect. Immun. (in press).

[16] R. L. Lemieux, *Methods Carbohydr. Chem*, 2 (1963) 221–222.

[17] P. Kovac, in "*Modern Methods in Carbohydrate Synthesis*" (s. H. Kan and R. A. O'Neill, ads.), pp. 55–81. Harwood Academic Publishers, Amsterdam, 1996.

[18] K. C. Nicolaou and H. Ueno, in "*Preparative Carbohydrate Chemistry*" (S. Hanessian, ed.), p. 313–338, Marcel Dekker, Inc., New York, N.Y., 1996.

[19] T. Norberg, in "*Modern Methods in Carbonhydrate Synthesis*" (S. H. Khan and R. A. O'Neill, eds.), p. 82–106. Harwood Academic Publishers, GmbH, Amsterdam, 1996.

[20] R. R. Schmidt, in "*Modern Methods in Carbohydrate Synthesis*" (S. H. Khan and R. A. O'Neill, eds), p. 20–54. Harwood Academic Publishers, GmbH, Amsterdam, 1996.

[21] S. H. Khan and R. A. O'Neill, (eds.), "Modern Methods in Carbohydrate Synthesis." Harwood Academic Publishers, Amsterdam, 1996.

[22] S. Hanessian, (ed.), "*Preparative Carbohydrate Chemistry.*" Marcel Dekker, Inc., New York, N.Y., 1996.

[23] R. L. Whistler and M. L. Wolfrom, (eds.), "*Methods in Carbohydrate Chemistry*", New York, N.Y., 1963.

[24] P. Fugedi and P. Nanasi, *J. Carbohydr. Nucleosides, Nucleotides*, 8 (1981) 547–555.

[25] H. Flowers, *Methods in Enzymology*, 138 (1987) 359–404.

[26] P. Fugedi, P. J. Garegg, H. Lonn, and T. Norberg, *Glycoconjugate J.*, 4 (1987) 97–108.

[27] R. L. Halcomb and C. H. Wong, *Current opinion in Structural Biology*, 3 (1993) 694–700.

[28] O. Kanie, *Current Opinion in Structural Biology*, 2 (1992) 674–681.

[29] S. H. Khan and O. Hindsgaul, in "*Molecular Glycobiology*" (M. Fukuda and O. Hindsgaul, eds.), p. 206–229, JRL Press, Oxford, 1994.

[30] H. Paulsen, *Angew. Chem. Int. Ed. Engl.*, 21 (1982) 155–173.

[31] H. Paulsen, In "*Organic synthesis: and interdisciplinary challenge*" (H. P. J. Streith, and G. Schill, ed.), p. 317–335, 1985.

[32] H. Paulsen, in "*New synthetic methodology and functionally interesting compounds*", p. 243–270. Kodansha, Ltd., Tokyo, 1986.

[33] R. Roy, F. D. Tropper, S. Cao, and J. M. Kim, ACS Symp. Ser., 659 (1997) 163–180.

[34] R. R. Schmidt, *Angew. Chem. Int. Ed. Engl.*, 25 (1986) 212–235.

[35] K. Toshima and K. Tatsuta, *Chem. Rev.*, 93 (1993) 1503–1531.

[36] D. M. Whitfield and S. P. Douglas, *Glycoconjugate J.*, 13 (1996) 5–17.

[37] R. Binkley, F., "*Modern Carbohydrate Chemistry*", p. 343, New York, N.Y., 1988.

[38] R. T. Lee, T.-C. Wong, R. Lee, L. Yue, and Y. C. Lee, *Biochemistry*, 28 (1989) 1856–1861.

[39] R. T. Lee and Y. C. Lee, *Biochemistry*, 19 (1980) 156–163.

We claim:

1. A composition having the general formula (I):

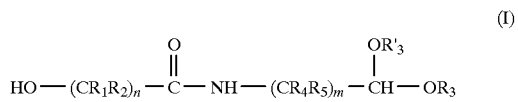

in which n and m are each independently an integer of from 1 to 12, $R_1$ and $R_2$ are each independently H, lower alkyl, a hydroxyl group, $R_4$ and $R_5$ are each independently H, lower alkyl, a hydroxyl group, $R_3$ and $R'_3$ are each independently an optionally substituted lower alkyl or $R_3$ and $R'_3$ can be joined to form an optionally substituted cyclic moiety having from 2 to 5 carbon atoms.

2. The composition of claim 1, wherein n is from 3 to 12 and m is from 1 to 10, $R_1$, $R_2$, $R_4$ and $R_5$ are each independently H, optionally substituted $C_1$–$C_3$ alkyl, or an hydroxyl group and $R_3$ and $R_3'$ are each independently a $C_1$–$C_3$ alkyl or $R_3$ and $R_3'$ are joined to form an optionally substituted cyclic moiety having 2 to 4 carbon atoms.

3. The composition of claim 1, wherein n is from 4 to 8, m is from 1 to 3, $R_1$, $R_2$, $R_4$ and $R_5$ and each independently H, optionally substituted $C_1$–$C_2$ alkyl or hydroxyl and $R_3$ and $R_3'$ are each independently optionally substituted $C_1$–$C_2$ alkyl or $R_3$ and $R_3'$ are joined to form an optionally substituted cyclic moiety having 2 to 3 carbon atoms.

4. The composition according to claim 1, having the formula:

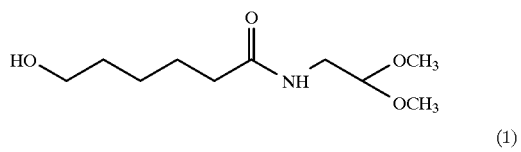

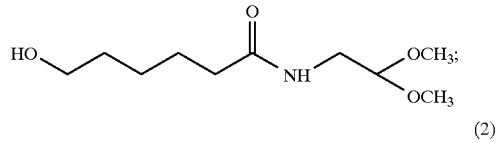

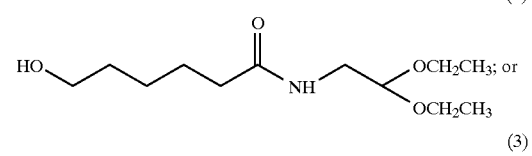

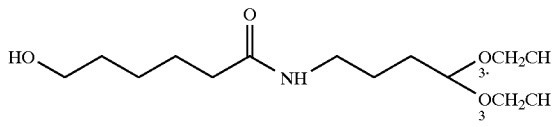

5. A composition having the general formula II:

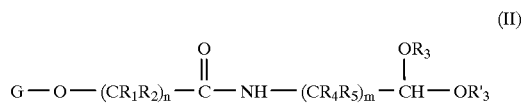

in which G is the radical of a glycoside wherein the glycoside is a mono, oligo or polysaccharide and n and m are each independently an integer of from 1 to 12, $R_1$ and $R_2$ are each independently H, lower alkyl, a hydroxyl group, $R_4$ and $R_5$ are each independently H, lower alkyl, a hydroxyl group, $R_3$ and $R'_3$ are each independently an optionally substituted lower alkyl or $R_3$ and $R'_3$ can be joined to form an optionally substituted cyclic moiety having from 2 to 5 carbon atoms.

6. The composition according to claim 5, wherein n is from 3 to 12 and m is from 1 to 10, $R_1$, $R_2$, $R_4$ and $R_5$ are each independently H, optionally substituted $C_1$–$C_3$ alkyl, or an hydroxyl group and $R_3$ and $R_3'$ are each independently a $C_1$–$C_3$ alkyl or $R_3$ and $R_3'$ are joined to form an optionally substituted cyclic moiety having 2 to 4 carbon atoms.

7. The composition according to claim 5, wherein n is from 4 to 8, m is from 1 to 3, $R_1$, $R_2$, $R_4$ and $R_5$ and each independently H, optionally substituted $C_1$–$C_2$ alkyl or hydroxyl and $R_3$ and $R_3'$ are each independently optionally substituted $C_1$–$C_2$ alkyl or $R_3$ and $R_3'$ are joined to form an optionally substituted cyclic moiety having 2 to 3 carbon atoms.

8. The composition according to claim 5, having the formula:

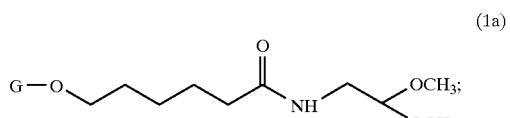

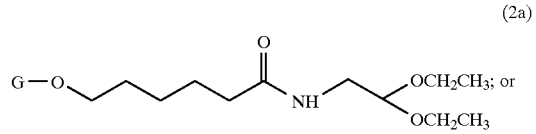

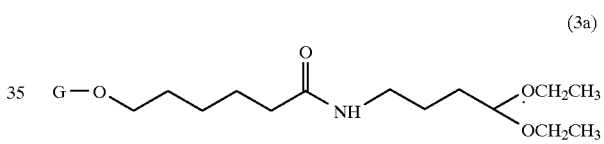

9. A composition having the general formula IV:

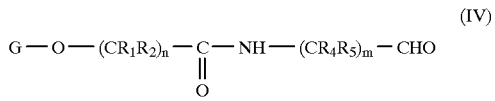

in which G is the radical of a glycoside wherein the glycoside is a mono, oligo or polysaccharide and n and m are each independently an integer of from 1 to 12 and $R_1$ and $R_2$ are each independently H, lower alkyl, hydroxyl group, $R_4$ and $R_5$ are each independently H, lower alkyl or a hydroxyl group.

10. The composition according to claim 9, wherein n is from 3 to 12 and m is from 1 to 10 and $R_1$, $R_2$, $R_4$ and $R_5$ are each independently H, optionally substituted $C_1$–$C_3$ alkyl, or an hydroxyl group.

11. The composition according to claim 9, wherein n is from 4 to 8, m is from 1 to 3 and $R_1$, $R_2$, $R_4$ and $R_5$ and each independently H, optionally substituted $C_1$–$C_2$ alkyl or hydroxyl.

12. The composition according to claim 9, having the formula:

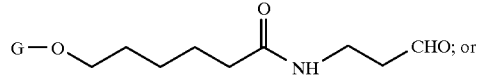

-continued

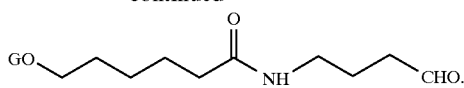

13. A composition having the general formula (VI)

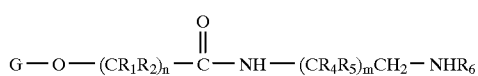
(VI)

in which G is the radical of a glycoside wherein the glycoside is a mono, oligo or polysaccharide and n and m are each independently an integer of from 1 to 12, $R_1$ and $R_2$ are each independently H, lower alkyl, a hydroxyl group, $R_4$ and $R_5$ are each independently H, lower alkyl or a hydroxyl group, and $R_6$ is the residue of an amine group-containing carrier.

14. The composition according to claim 13 wherein n is from 3 to 12 and m is from 1 to 10 and $R_1$, $R_2$, $R_4$ and $R_5$ are each independently H, optionally substituted $C_1$–$C_3$ alkyl, or an hydroxyl group.

15. The composition according to claim 13, wherein n is from 4 to 8, m is from 1 to 3 and $R_1$, $R_2$, $R_4$ and $R_5$ and each independently H, optionally substituted $C_1$–$C_2$ alkyl or hydroxyl.

16. The composition according to claim 13, having the formula:

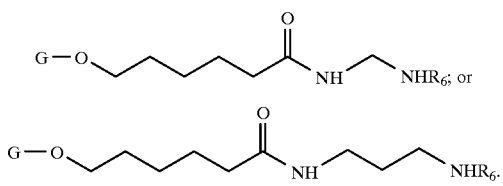

17. A composition according to claim 13, wherein the carrier is a synthetic or natural carrier material which is water-soluble, water-dispersible or water-insoluble.

18. A composition according to claim 17, wherein the carrier material is polymeric.

19. A composition according to claim 18, wherein the carrier material is a natural or synthetic peptide, an oligopeptide, a polypeptide or a protein.

20. A composition according to claim 18, wherein the carrier material is an aminoalkyl Sepharose, aminopropyl glass or an oligosaccharide or a polysaccharide having at least one aminoalkyl group.

21. A composition according to claim 17, wherein the oligopeptide, polypeptide, or protein is immunogenic.

22. A composition according to claim 18, wherein the oligosaccharide, polysaccharide or lipopolysaccharide is immunogenic.

23. A vaccine comprising an effective amount of a composition according to claim 13 and a physiologically acceptable carrier.

24. A method for the coupling of an aldehyde group-containing material to an amino group-containing material comprising the steps of a) providing a glycosyl donor derived from a mono, oligo, poly or a saccharide fragment of a lipopolysaccharide;

b) reacting the glycosyl donor with a linker of formula I

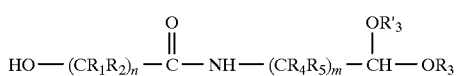
(I)

in which n and m are each independently an integer of from 1 to 12, $R_1$ and $R_2$ are each independently H, lower alkyl, a hydroxyl group, $R_4$ and $R_5$ are each independently H, lower alkyl, a hydroxyl group, $R_3$ and $R'_3$ are each independently an optionally substituted lower alkyl or $R_3$ and $R'_3$ can be joined to form an optionally substituted cyclic moiety having from 2 to 5 carbon atoms to give an intermediate in which a residue of the protected saccharide is coupled to the linker compound via its hydroxyl group;

b') subjecting the intermediate of step b) to deprotection of the saccharide to generate an intermediate having the saccharide moiety deprotected but the aldehyde function still protected;

c) subjecting the intermediate of step b') to deprotection to generate a terminal aldehydo group;

d) selecting an amino group-containing carrier material having at least one primary amino group and reacting the amino group of the carrier material with the aldehydo group of the material formed in step c) to provide a Schiff base;

e) reducing the Schiff base of step d) and;

f) isolating the linker coupled material.

25. A method according to claim 24, wherein the carrier material is polymeric.

26. A method according to claim 25, wherein the carrier material is a natural or synthetic peptide or oligopeptide, polypeptide or protein.

27. A method according to claim 25, wherein the carrier material is an aminoalkyl Sepharose, aminopropyl glass or an oligosaccharide or a polysaccharide having at least one aminoalkyl group.

28. A method of making a composition according to claim 1 comprising reacting a lactone of the general formula VII

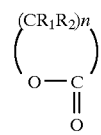
(VII)

with an amine-containing protected aldehyde of the general formula (VIII):

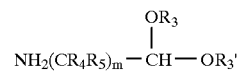
(VIII)

and isolating the amide containing protected aldehyde of the general formula (I):

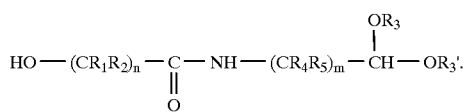

29. A method according to claim 28, wherein n is from 3 to 12 and m is from 1 to 10, $R_1$, $R_2$, $R_4$ and $R_5$ are each independently H, optionally substituted $C_1$–$C_3$ alkyl, or an hydroxyl group and $R_3$ and $R_3'$ are each independently a $C_1$–$C_3$ alkyl or $R_3$ and $R_3'$ are joined to form an optionally substituted cyclic moiety having 2 to 4 carbon atoms.

30. A method according to claim 28, wherein n is from 4 to 8, m is from 1 to 3, $R_1$, $R_2$, $R_4$ and $R_5$ and each independently H, optionally substituted $C_1$–$C_2$ alkyl or hydroxyl and $R_3$ and $R_3'$ are each independently optionally substituted $C_1$–$C_2$ alkyl or $R_3$ and $R_3'$ are joined to form an optionally substituted cyclic moiety having 2 to 3 carbon atoms.

31. A method according to claim 28, wherein the lactone of formula VII is ε-caprolactone, δ-butyrolactone, δ-caprolactone or β-propiolactone.

* * * * *